United States Patent [19]

Draenert

[11] Patent Number: 4,842,603
[45] Date of Patent: Jun. 27, 1989

[54] MATERIALS FOR IMPLANTATION COMPRISING A POLYACRYLATE CONTAINING SPHERICAL TRICALCIUM PHOSPHATE PARTICLES

[75] Inventor: Klaus Draenert, Ottobrunn, Fed. Rep. of Germany

[73] Assignee: Merck Patent Gesellschaft Mit Beschränkter Haftung, Darmstadt, Fed. Rep. of Germany

[21] Appl. No.: 14,418

[22] Filed: Feb. 12, 1987

Related U.S. Application Data

[63] Continuation of Ser. No. 711,504, Mar. 12, 1985.

[30] Foreign Application Priority Data

Jul. 7, 1983 [DE] Fed. Rep. of Germany ....... 3325111

[51] Int. Cl.$^4$ .......................... C08K 3/10; C08K 3/32; A61F 1/00
[52] U.S. Cl. ................. 623/16; 128/92 VP; 128/92 YQ; 428/307.3; 428/314.2; 428/319.7; 428/407; 433/201.1; 523/114; 523/115; 523/116
[58] Field of Search .......... 128/92 G, 92 VP, 92 YQ; 428/307.3, 314.2, 319.7, 407; 433/201.1; 523/114, 115, 116; 623/16

[56] References Cited

U.S. PATENT DOCUMENTS

| | | | |
|---|---|---|---|
| 4,202,055 | 5/1980 | Reiner et al. | 128/92 C |
| 4,373,217 | 2/1983 | Draenert | 523/115 |
| 4,548,959 | 10/1985 | Nagai et al. | 623/16 |
| 4,610,692 | 9/1986 | Eitenmuller et al. | 623/16 |
| 4,623,553 | 11/1986 | Ries et al. | 623/16 |
| 4,654,314 | 3/1987 | Takagi et al. | 623/16 |
| 4,655,777 | 4/1987 | Dunn et al. | 623/16 |
| 4,661,536 | 4/1987 | Dorman et al. | 623/16 |

*Primary Examiner*—Herbert J. Lilling
*Attorney, Agent, or Firm*—Millen, White & Zelano

[57] ABSTRACT

Particles of absorbable filler based on tricalcium phosphate having a particle size between 50 and 300 μm, which predominantly have an approximately spherical shape, are used in materials for implantation, which are based on polyacrylates, for the management of bone defects.

10 Claims, No Drawings

MATERIALS FOR IMPLANTATION COMPRISING A POLYACRYLATE CONTAINING SPHERICAL TRICALCIUM PHOSPHATE PARTICLES

This is a continuation of application Ser. No. 711,504 filed Mar. 12, 1985.

BACKGROUND OF THE INVENTION

The invention relates to materials for implantation which are based on polyacrylates and which can be used, in particular, as materials for replacement of bone, for uniting bone and for anchoring prostheses.

The admixture of absorbable tricalcium phosphate to these materials for implantation, which are also known as bone cements, is disclosed, in European Pat. No. A1 16906, in order to provide in the implant, by the onset of absorption at the margin of the implant, channels into which the bone tissue can grow. This leads to the implant meshing together with the surrounding bone and thus to improved long-term stability. By use of relatively small amounts of tricalcium phosphate, of from 5 to 35 percent by weight, in particular about 20 to 25 percent by weight, there is essentially the development of only marginal porosity, since the absorbable particles of filler in the implant are not so closely packed that they come into contact with one another, and thus complete absorption starting from the margin would be possible.

It has now emerged that the particles of filler located inside the implant can be the starting point for disintegration of the implant. Apparently, the particles of tricalcium phosphate do not participate in elastic movements of the acrylate polymer, which take place when the prosthesis which has been cemented in is subjected to loading and unloading, so that stress situations arise at the incorporated particles and, in the long term, these destroy the structure of the polymer.

A solution to this problem taking the form of increasing the proportion of filler to such an extent that the particles come into contact with one another and thus can be completely absorbed starting from the margin is inadvisable since this would lead to a great reduction in the short-term stability of the implant itself. On the other hand, with a marginal porosity the anchoring of the implant which is achieved is sufficiently good for it to be possible to dispense with bone tissue growing completely through the implant with the aim of good longterm stability.

Thus, the object was to find a filling material which is based on tricalcium phosphate and which can be admixed to the cement in the amounts and particle sizes disclosed in European Patent A1 16906 but which essentially avoids stress situations between particles of filler and the polymer composition.

SUMMARY OF THE INVENTION

This object has been achieved by the present invention.

Thus the invention relates to materials for implantation which are based on polyacrylates which contain 5 to 35 percent by weight of particles based on absorbable tricalcium phosphate, having a particle size between 20 and 300 $\mu$m, which are characterized in that these particles predominantly have an approximately spherical shape.

The invention also relates to particles of absorbable filler, based on tricalcium phosphate, for use in bone cements, which are characterized in that they have a particle size between 50 and 300 $\mu$m, and predominantly have an approximately spherical shape.

DETAILED DISCUSSION

The invention entails a number of advantages. The reduction in the exposure to stress, which derives from an irregular particle having corners and edges, during elastic movements of the cement is very considerable. In contrast, with an essentially round particle, it is possible to a certain extent for displacement of the interfaces between the particles of filler and acrylate polymer to take place without this leading to stress on the polymer. In the case of pure pressure loading of the cement, the spherical shape is also a considerable advantage since in this instance the pressure is both taken up and transmitted over a large area, distributed equally, and is not restricted to a few exposed points.

The fillers according to the invention can be prepared by a variety of ways. The preferred starting material is a highly porous tricalcium phosphate having a porosity of about 50 to 80%. It has emerged that a highly porous tricalcium phosphate is absorbed far more rapidly than a tricalcium phospate whose pore volume has been reduced by sintering. In order to prevent, during mixing of the componets of the bone cement, liquid monomer being taken up in the pores of the tricalcium phosphate and plymerization taking place there, the pores are filled with an absorbable material which is tolerated by the body and is immiscible with the acrylate monomer. This filling of the pores can be carried out by rapidly absorbable substances, such as, for example, glycerol, but it is also possible to use for this purpose absorbable polymers, such as, for example, polylactides, polyglycolides, polyhydroxycarboxylic acids or polyaminoacids. Filling the pores with absorbable polymers has the advantage that the particles have greater mechanical stability, which is essential, especially with respect to the particles remaining inside the bone cement.

Another preferred method for the preparation of the fillers according to the invention comprises starting from a tricalcium phosphate in the form of a finely divided powder and having a particle size in approximately the range 1 to 5 $\mu$m, and bonding this, using an absorable material which is tolerated by the body, to give essentially spherical particles of size 20 to 300 $\mu$m, in particular about 150 to 250 $\mu$m. Examples of suitable matrix materials for the tricalcium phosphate in the form of a powder are absorbable polymers, such as polylactide, polyglycolide, polyhydroxycarboxylic acids, polyaminoacids and polyesters.

These particles of filler which are based on tricalcium phosphate in the form of a powder are particularly advantageous, since the elasticity of this material composed of a polymer matrix and tricalcium phosphate powder is essentially similar to that of the acrylate polymer which forms the bone cement. Hence, during elastic movement of the bone cement in the body, the particles of filler, which are essentially isoelastic, can deform in the same manner, so that it is impossible for there to be any surface displacement between the particles of filler and the bone cement. An optimal mechanical compatibility of the filler with the cement is achieved in this manner.

It would be conceivable, based on the purely mechanical properties of the cement, to prepare the fillers completely of an absorbable polymer. However, in respect of the biological properties of the implant, the presence of tricalcium phosphate is very desirable. Hence, as a rule, the particles of filler according to the invention contain about 20 to 90% tricalcium phosphate, in particular about 30 to 50%.

The term tricalcium phospate which is used in the present application is to be understood to be a term comprehending a number of different materials which can essentially be described by the chemical formula $Ca_3(PO_4)_2$, the ratio of calcium to phosphorus being approximately 3:2.

However, apart from pure tricalcium phosphates, such as, for example, α- or β-whitlockite, it is intended to comprise also those materials which are only approximately described by the formula $Ca_3(PO_4)_2$, such as, for example, apatites or phosphorite. Hydroxyapatite is a particularly preferred material. In any event, the tricalcium phosphate should be absorbable in the body.

The fillers according to the invention are incorporated in bone cements in analogy to the processes described in European Pat. No. A1 16906, and are used for the purposes described in this patent. Due to the advantages mentioned, materials for implantation which contain the fillers according to the invention have a considerably improved long-term stability, so that a considerable advance in the area of materials for implantation is achieved with the present invention.

What is claimed is:

1. In an implantation material comprising a polyacrylate which contains 5 to 35 percent by weight of non-closely packed particles comprising absorbable tricalcium phosphate having a particle size between 20 and 300 μm, said particles being packed within the polyacrylate so that complete absorption of the particles does not occur after implantation, the improvement wherein said particles predominantly have an approximately spherical shape.

2. The material of claim 1, wherein the particles are composed of a highly porous tricalcium phospate whose pores are filled with an absorbable substance which is tolerated by the body.

3. The materials of claim 1, wherein the particles consist of tricalcium phosphate powder which has been bonded with an absorbable substance which is tolerated by the body.

4. The materials of claim 2 or 3, wherein a polyaminoacid or glycerol is used as the absorbable substance which is tolerated by the body.

5. The materials of claim 2, wherein the tricalcium phosphate used has a porosity of 50 to 80%.

6. In a method of treating a bone defect comprising implanting a bone cement material, the improvement wherein the material is that of claim 1.

7. In a method of anchoring a prosthesis comprising contacting it with a bone cement, the improvement wherein the bone cement is that of claim 1.

8. In a bone cement comprising a polyacrylate containing 5 to 35 percent by weight of non-closely packed filler particles, said particles being packed within the polyacrylate so that complete absorption of the particles does not occur after implantation, said filler particles comprising absorbable tricalcium phosphate and having a particle size of 20–300 μm, the improvement wherein said particle have a substantially spherical shape.

9. In a bone cement for cementing a prospthesis to bone tissue, said bone cement comprising a polyacrylate containing 5 to 35 percent by weight of non-closely pakced filler particles, said particles being packed within the polyacrylate so that complete absorption of the particles does not occur after implantation, said filler particles comprising absorbable tricalcium phosphate and having a particles size of 20–300 μm, and said bone cement being separate from a prosthesis which is to be implanted in bone tissue, the improvement wherein said filler particles have a substantially spherical shape.

10. In an implantation material comprising a polyacrylate which contains 5 to 35% by weight of non-closely packed particles comprising absorbable tricalcium phosphate having a particle size between 20 and 300 μm, said particles being packed within the polyacrylate so that complete absorption of the particles does not occur after implantation, the improvement wherein said particles predominantly have an essentially round shape.

* * * * *